United States Patent
Makio et al.

(10) Patent No.: US 11,987,538 B2
(45) Date of Patent: May 21, 2024

(54) METHOD FOR PRODUCING CYCLIC OLEFIN COMPOUND

(71) Applicant: MITSUI CHEMICALS, INC., Tokyo (JP)

(72) Inventors: Haruyuki Makio, Chiba (JP); Takaaki Yano, Ichihara (JP); Akira Matsuura, Higashi-osaka (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 18/000,534

(22) PCT Filed: Jun. 10, 2021

(86) PCT No.: PCT/JP2021/022062
§ 371 (c)(1),
(2) Date: Dec. 2, 2022

(87) PCT Pub. No.: WO2021/261264
PCT Pub. Date: Dec. 30, 2021

(65) Prior Publication Data
US 2023/0219868 A1 Jul. 13, 2023

(30) Foreign Application Priority Data
Jun. 26, 2020 (JP) .................. 2020-110761

(51) Int. Cl.
*C07C 1/32* (2006.01)
*B01J 31/24* (2006.01)
*C07C 1/207* (2006.01)

(52) U.S. Cl.
CPC .......... *C07C 1/325* (2013.01); *B01J 31/2438* (2013.01); *B01J 2231/64* (2013.01); *C07C 2603/66* (2017.05)

(58) Field of Classification Search
CPC ....... C07C 1/207; C07C 1/2078; C07C 1/325; C07C 2603/66; C07C 2523/755; C07C 2531/04; C07C 2531/20; B01J 31/2438; B01J 2231/64
See application file for complete search history.

(56) References Cited

U.S. PATENT DOCUMENTS 4,012,399 A * 3/1977 Hechenbleikner ... C08K 5/0091
556/18
9,024,103 B2 * 5/2015 Ishihara ................ C07C 1/2078
585/638

FOREIGN PATENT DOCUMENTS

JP 2008-239584 A 10/2008
WO 2008062553 A1 5/2008

OTHER PUBLICATIONS

Meriwether et al. (Journal of the American Chemical Society 81.16 (1959): 4200-4208) (Year: 1959).*
Toman et al. (Journal of the American Chemical Society 94.8 (1972): 2669-2676) (Year: 1972).*
Aresta et al. (Inorganica Chimica Acta 12.1 (1975): 167-178) (Year: 1975).*
Vasapollo et al. (Inorganica Chimica Acta 37 (1979): 455-456) (Year: 1979).*
John et al. ("Anhydride-Additive-Free Nickel-Catalyzed Deoxygenation of Carboxylic Acids to Olefins." Organometallics (2017), 36, 506-509) (Year: 2017).*
Trost et al., "Transition Metal Mediated Eliminations in Anhydrides and Thioanhydrides", Tetrahedron Letters, 1971, vol. 12, Issue 28, pp. 2603-2607. (Cited in Office Action dated Jul. 11, 2023, in corresponding Japanese Patent Application No. 2022-531733).

* cited by examiner

*Primary Examiner* — In Suk C Bullock
*Assistant Examiner* — Jason Y Chong
(74) *Attorney, Agent, or Firm* — BUCHANAN, INGERSOLL & ROONEY PC

(57) ABSTRACT

Provided is a method for producing a cyclic olefin compound, including a step of producing a cyclic olefin compound by acting a divalent nickel complex represented by General Formula (1) to decarbonylate and decarboxylate an alicyclic dicarboxylic acid anhydride, in which the divalent nickel complex includes at least one specific anionic ligand Y:

$$Ni(Y)_m(L)_n \qquad (1)$$

wherein Ni is divalent nickel, Y is an anionic monodentate or polydentate ligand and has at least one Ni-E covalent bond, E is a heteroatom or a π-bonding group, m is 1 or 2, L is a neutral ligand, and n is a real number of 0 to 6.

17 Claims, No Drawings

METHOD FOR PRODUCING CYCLIC OLEFIN COMPOUND

TECHNICAL FIELD

The present invention relates to a method for producing a cyclic olefin compound.

BACKGROUND ART

A cyclic olefin compound is useful as a raw material for a cyclic olefin (co)polymer (COC, COP) which is obtained by copolymerization of a cyclic olefin with lower olefins such as ethylene or ring-opening metathesis polymerization of a cyclic olefin. Various methods have been known for producing the cyclic olefin compound, and among these, there is (1) decarbonylation and decarboxylation reaction of an alicyclic dicarboxylic acid anhydride or (2) oxidative decarboxylation reaction of a dicarboxylic acid derivative obtained by hydrolysis of an alicyclic dicarboxylic acid anhydride.

The alicyclic dicarboxylic acid anhydride used as a raw material for these reactions can be obtained by a Diels-Alder reaction between a conjugated diene compound and maleic anhydride and its derivatives. In general, as the maleic anhydrides exhibit high reactivity in the Diels-Alder reaction, an adduct is often obtained in a good yield. Therefore, in a case where the decarboxylation and/or decarboxylation can be efficiently carried out from these alicyclic dicarboxylic acid anhydrides or dicarboxylic acid derivatives obtained by hydrolysis thereof, it can be expected that cyclic olefin compounds having various structures can be synthesized in high yields by combining various diene compounds and maleic anhydrides.

Examples of the technique relating to the method for producing such a cyclic olefin compound include those disclosed in Patent Document 1 (International Publication No. WO 2008/062553).

Patent Document 1 discloses a method for producing a cyclic olefin compound represented by a specific chemical formula via decarbonylation and decarboxylation of an alicyclic dicarboxylic acid anhydride represented by a specific chemical formula, using a nickel complex as a catalyst in the coexistence of a compound which can be a ligand, and removing the generated cyclic olefin compound to an outside of the reaction system.

Patent Document 1 discloses that the above-described production method enables significant reduction of an amount of the nickel complex used as a catalyst, and helps to solve problems in known methods, such as high cost due to a large amount of expensive raw materials, low product yields, complicated product separation and purification, and discharge of a large amount of wastes.

RELATED DOCUMENT

Patent Document

[Patent Document 1] International Publication No. WO 2008/062553

SUMMARY OF THE INVENTION

Technical Problem

According to studies by the present inventors, it has been found that since the nickel complex catalyst used in Patent Document 1 is in effect a zero-valent compound, it becomes expensive and so unstable that it decomposes in the atmosphere, and that the method for producing a cyclic olefin compound disclosed in Patent Document 1 has room for improvement from the viewpoint of operation and stability in producing the cyclic olefin compound.

The present invention has been made in view of the above-described circumstances, and an object of the present invention is to provide a method for producing a cyclic olefin compound, in which, by using a specific divalent nickel complex, a cyclic olefin compound can be stably produced even in a case where the nickel complex is exposed to the atmosphere.

Solution to Problem

That is, according to the present invention, the following methods for producing a cyclic olefin compound are provided.

[1]

A method for producing a cyclic olefin compound, including:

a step of producing a cyclic olefin compound by acting a divalent nickel complex represented by General Formula (1) to decarbonylate and decarboxylate an alicyclic dicarboxylic acid anhydride, in which the divalent nickel complex includes at least one anionic ligand Y represented by any of General Formulae (2) to (7), (X1), and (Y1), $$\text{Ni}(Y)_m(L)_n \qquad (1)$$

(here, Ni is divalent nickel, Y is an anionic monodentate or polydentate ligand and has at least one Ni-E covalent bond, E is a heteroatom or a π-bonding group, m is 1 or 2, L is a neutral ligand, and n is a real number of 0 to 6)

[Chem. 1]

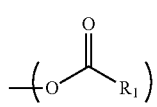

(2)

($R_1$ is a hydrogen atom or a hydrocarbon group which may have a substituent)

[Chem. 2]

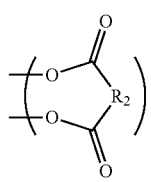

(3)

($R_2$ is a divalent hydrocarbon group which may have a substituent)

[Chem. 3]

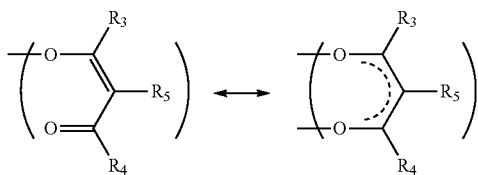
(4)

($R_3$, $R_4$, and $R_5$ are hydrocarbon groups which may have a substituent, $R_3$ and $R_5$ or $R_4$ and $R_5$ may be bonded to each other to form a ring, and $R_3$, $R_4$, and $R_5$ may be hydrogen atoms)

[Chem. 4]

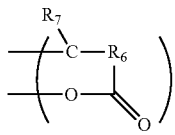
(5)

($R_6$ is a divalent hydrocarbon group which may have a substituent, $R_7$ is a hydrogen atom, a hydrocarbon group which may have a substituent, or an oxo group, and in a case where $R_7$ is a hydrocarbon group, $R_7$ may be bonded to $R_6$ to form a ring)

[Chem. 5]

(6)

(Z' is halogen or OH)

[Chem. 6]

(7)

(Ox is an oxoacid selected from $NO_3^{-}$, $CO_3^{2-}$, and $PO_4^{3-}$)

[Chem. 7]

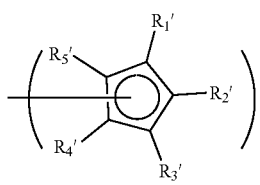
(X1)

($R_1'$, $R_2'$, $R_3'$, $R_4'$, and $R_5'$ are each independently a hydrogen atom or a hydrocarbon group which may have a substituent)

[Chem. 8]

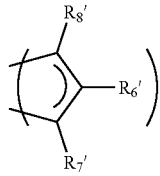
(Y1)

($R_6'$, $R_7'$, and $R_8'$ are each independently a hydrogen atom or a hydrocarbon group which may have a substituent).

[2]

The method for producing a cyclic olefin compound according to [1],
in which the divalent nickel complex includes at least one anionic ligand Y represented by any of General Formulae (9), (11) to (13), and (Z1), and Formulae (8) and (10),

[Chem. 9]

(8)

[Chem. 10]

(9)

(X is a group of non-metal atoms required to form a ring, and R and R' are each independently a hydrogen atom or a hydrocarbon group which may have a substituent)

[Chem. 11]

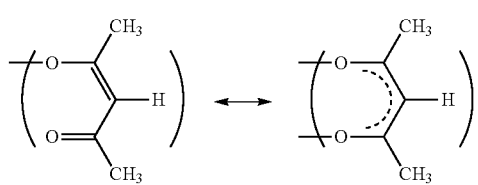
(10)

[Chem. 12]

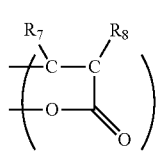
(11)

($R_7$ and $R_8$ are each independently a hydrogen atom or a hydrocarbon group which may have a substituent, and $R_7$ and $R_8$ may be bonded to each other to form a ring)

[Chem. 13]

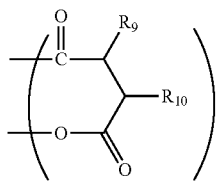
(12)

($R_9$ and $R_{10}$ are each independently a hydrogen atom or a hydrocarbon group which may have a substituent, and $R_9$ and $R_{10}$ may be bonded to each other to form a ring)

[Chem. 14]

(13)

($Z''$ is Cl or Br)

[Chem. 15]

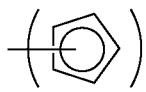
(Z1)

[3]

The method for producing a cyclic olefin compound according to [1] or [2],
in which, in the step of producing a cyclic olefin compound, a compound which can be a ligand for the nickel complex is further present.

[4]

The method for producing a cyclic olefin compound according to [3],
in which, in the step of producing a cyclic olefin compound, the compound which can be a ligand is present in an amount of 10 to 500 mol with respect to 1 mol of the nickel complex.

[5]

The method for producing a cyclic olefin compound according to [3] or [4],
in which the compound which can be a ligand includes a phosphorus-containing compound.

[6]

The method for producing a cyclic olefin compound according to any one of [3] to [5],
in which the compound which can be a ligand includes at least one selected from a compound represented by General Formula (14) and a compound represented by General Formula (15),

[Chem. 16]

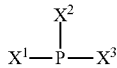
(14)

($X^1$, $X^2$, and $X^3$ are each independently a hydrocarbon group which may have a substituent)

[Chem. 17]

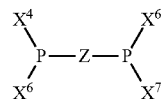
(15)

($X^4$, $X^5$, $X^6$, and $X^7$ are each independently a hydrocarbon group which may have a substituent, and Z is an alkylene group having 1 to 20 carbon atoms, an arylene group having 6 to 20 carbon atoms, a ferrocenylene group, or a binaphthylene group)

[7]

The method for producing a cyclic olefin compound according to any one of [3] to [6],
in which the compound which can be a ligand includes triphenylphosphine.

[8]

The method for producing a cyclic olefin compound according to any one of [1] to [7], further including:
a step of adding an alcohol compound.

[9]

The method for producing a cyclic olefin compound according to [8],
in which a boiling point of the alcohol compound is lower than a boiling point of the alicyclic dicarboxylic acid anhydride.

[10]

The method for producing a cyclic olefin compound according to any one of [1] to [9],
in which the alicyclic dicarboxylic acid anhydride includes at least one of a carboxylic acid compound or a carboxylic acid anhydride (excluding the alicyclic dicarboxylic acid anhydride) as an impurity.

[11]

The method for producing a cyclic olefin compound according to [10], further including:
a step of adding an alcohol compound; and
a step of contacting the alcohol compound with the impurity in a liquid phase to react the alcohol compound with the carboxylic acid compound or the carboxylic acid anhydride in the impurity, and removing an unreacted alcohol compound.

[12]

The method for producing a cyclic olefin compound according to [11],
in which a boiling point of the alcohol compound is lower than a boiling point of the alicyclic dicarboxylic acid anhydride.

[13]

The method for producing a cyclic olefin compound according to any one of [1] to [12],
in which the alicyclic dicarboxylic acid anhydride includes a compound represented by General Formula (16), and the cyclic olefin compound includes a compound represented by General Formula (17),

[Chem. 18]

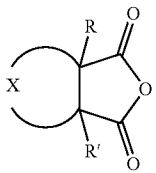

(16)

(X is a group of non-metal atoms required to form a ring, and R and R' are each independently a hydrogen atom or a hydrocarbon group which may have a substituent)

[Chem. 19]

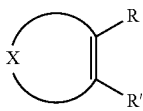

(17)

(X is a group of non-metal atoms required to form a ring, and R and R' are each independently a hydrogen atom or a hydrocarbon group which may have a substituent)

[14]

The method for producing a cyclic olefin compound according to any one of [1] to [13],
in which the alicyclic dicarboxylic acid anhydride includes 5,6-benzo-2,3-dicarboxylic acid anhydrides represented by General Formula (18),

[Chem. 20]

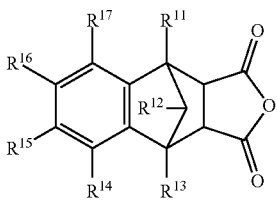

(18)

($R^{11}$, $R^{12}$, $R^{13}$, $R^{14}$, $R^{15}$, $R^{16}$, and $R^{17}$ are each independently a hydrogen atom or a substituent which may have a heteroatom)

[15]

The method for producing a cyclic olefin compound according to [14],
in which $R^{11}$, $R^{12}$, $R^{13}$, $R^{14}$, $R^{15}$, $R^{16}$, and $R^{17}$ in General Formula (18) are all hydrogens.

[16]

The method for producing a cyclic olefin compound according to any one of [1] to [13],
in which the alicyclic dicarboxylic acid anhydride includes a dicarboxylic acid anhydride represented by General Formula (19),

[Chem. 21]

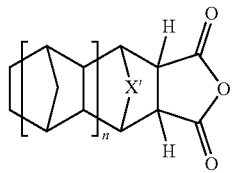

(19)

(n is 0 or 1, and X' is 0 or $CH_2$)

[17]

The method for producing a cyclic olefin compound according to any one of [1] to [16],
in which the step of producing a cyclic olefin compound is performed while removing the generated cyclic olefin compound to an outside of a reaction system.

Advantageous Effects of Invention

According to the present invention, a method for producing a cyclic olefin compound, in which a cyclic olefin compound can be stably produced even in a case where the nickel complex is exposed to the atmosphere, is provided.

DESCRIPTION OF EMBODIMENTS

Hereinafter, embodiments of the present invention will be described in detail. In the present embodiment, "A to B" indicating a numerical range represents equal to or more than A and equal to or less than B, unless otherwise specified.

A method for producing a cyclic olefin compound according to the present embodiment includes a step of producing a cyclic olefin compound by applying a divalent nickel complex represented by General Formula (1) to carry out decarbonylation and decarboxylation of an alicyclic dicarboxylic acid anhydride, in which the divalent nickel complex includes at least one anionic ligand Y represented by any of General Formulae (2) to (7), (X1), and (Y1).

$$Ni(Y)_m(L)_n \qquad (1)$$

Here, Ni is divalent nickel, Y is an anionic monodentate or polydentate ligand and has at least one Ni-E covalent bond, E is a heteroatom or a π-bonding group, m is 1 or 2, L is a neutral ligand, and n is a real number of 0 to 6.

Since the above-described divalent nickel complex represented by General Formula (1) is stable even in a case of being exposed to the atmosphere including oxygen and moisture, according to the method for producing a cyclic olefin compound according to the present embodiment, the cyclic olefin compound can be stably produced.

Further, since the above-described divalent nickel complex represented by General Formula (1) is easy to handle, easy to synthesize, and is inexpensive, the method for producing a cyclic olefin compound according to the present embodiment is suitable for mass production of the cyclic olefin compound.

E in General Formula (1) is preferably a carboxylate group or a cyclopentadienyl group.

Examples of the π-bonding group include a cyclopentadienyl group and a derivative thereof, and n-allyl group and a derivative thereof. In a case where E is a π-bonding group, examples of the above-described divalent nickel complex include nickelocene and a derivative thereof, and bis(n-allyl) nickel and a derivative thereof.

Since it improves stability against water and oxygen, E in General Formula (1) is more preferably a heteroatom.

L is a neutral compound including phosphorus, nitrogen, sulfur, oxygen, or the like, and examples thereof include phosphines, amines, ethers, thioethers, alcohol, thiol, water, and carbon monoxide. Among these, water, phosphines, or carbon monoxide is preferable.

[Chem. 22]

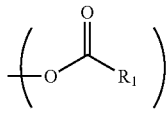

(2)

$R_1$ is a hydrogen atom or a hydrocarbon group which may have a substituent. Examples of the hydrocarbon group include groups having 1 to 30 carbon atoms, for example, an alkyl group such as a methyl group, an ethyl group, and a propyl group; an alkenyl group such as a vinyl group and an aryl group; an alkynyl group such as an ethynyl group and a propynyl group; an allyl group such as a phenyl group and a tolyl group; an aralkyl group such as a benzyl group and a phenethyl group; and a long-chain alkyl group such as a lauryl group and a stearyl group. Among these, $R_1$ is preferably a hydrogen atom or an alkyl group, and more preferably a hydrogen atom, a methyl group, or an ethyl group.

Examples of the substituent include a halogen, an alkyl group, an alkenyl group, an alkynyl group, an aryl group, an aralkyl group, an alkoxy group, an alkoxycarbonyl group, an alkylcarbonyloxy group, an acyl group, an alkylamino group, a carbamoyl group, a nitro group, a nitroso group, a cyano group, an alkylthio group, a sulfinyl group, a sulfonyl group, and a silyl group. In addition, among these substituents, adjacent substituents may be crosslinked to form a ring including the bonded carbon atom.

[Chem. 23]

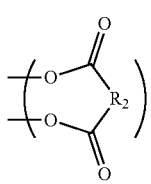

(3)

$R_2$ is a divalent hydrocarbon group which may have a substituent. Examples of the divalent hydrocarbon group include methylene, ethylene, trimethylene, vinylene, 1,2-phenylene, 2,3-naphthalene, 1,2-cyclohexylene, 1,2-bicyclo[2,2,1]heptalene, and 1,4-dihydro-1,4-methano-2,3-naphthalene. Among these, $R_2$ is preferably 1,4-dihydro-1,4-methano-2,3-naphthalene.

[Chem. 24]

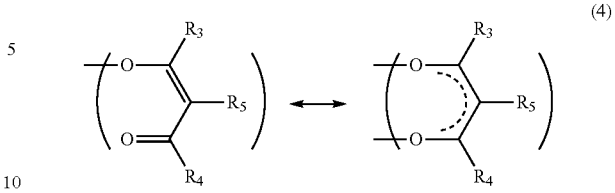

(4)

$R_3$, $R_4$, and $R_5$ are hydrocarbon groups which may have a substituent, and $R_3$ and $R_5$ or $R_4$ and $R_5$ may be bonded to each other to form a ring. In addition, $R_3$, $R_4$, and $R_5$ may be hydrogen atoms. Examples of the hydrocarbon group include groups having 1 to 8 carbon atoms, for example, an alkyl group such as a methyl group, an ethyl group, and a propyl group; an alkenyl group such as a vinyl group and an aryl group; an alkynyl group such as an ethynyl group and a propynyl group; an allyl group such as a phenyl group and a tolyl group; and an aralkyl group such as a benzyl group and a phenethyl group. Among these, $R_3$, $R_4$, and $R_5$ are preferably a hydrogen atom or an alkyl group, and more preferably a hydrogen atom, a methyl group, or an ethyl group.

Examples of the substituent include a halogen, an alkyl group, an alkenyl group, an alkynyl group, an aryl group, an aralkyl group, an alkoxy group, an alkoxycarbonyl group, an alkylcarbonyloxy group, an acyl group, an alkylamino group, a carbamoyl group, a nitro group, a nitroso group, a cyano group, an alkylthio group, a sulfinyl group, a sulfonyl group, and a silyl group. In addition, among these substituents, adjacent substituents may be crosslinked to form a ring including the bonded carbon atom.

[Chem. 25]

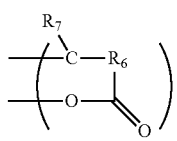

(5)

$R_6$ is a divalent hydrocarbon group which may have a substituent, and $R_7$ is a hydrogen atom, a hydrocarbon group which may have a substituent, or an oxo group. In a case where $R_7$ is a hydrocarbon group, $R_7$ may be bonded to $R_6$ to form a ring.

Examples of the divalent hydrocarbon group of $R_6$ include methylene, ethylene, and trimethylene groups. In addition, in combination with $R_7$—C—$R_6$, a double bond or a cyclic structure such as vinylene, 1,2-phenylene, 2,3-naphthalene, 1,2-cyclohexylene, 1,2-bicyclo[2,2,1]heptalene, and 1,4-dihydro-1,4-methano-2,3-naphthalene may be formed. Among these, ethylene, 1,2-bicyclo[2,2,1]heptalene, or 1,4-dihydro-1,4-methano-2,3-naphthalene is preferable.

Examples of the hydrocarbon group of $R_7$ include groups having 1 to 8 carbon atoms, for example, an alkyl group such as a methyl group, an ethyl group, and a propyl group; an alkenyl group such as a vinyl group and an aryl group; an alkynyl group such as an ethynyl group and a propynyl group; an allyl group such as a phenyl group and a tolyl group; and an aralkyl group such as a benzyl group and a phenethyl group. Among these, $R_7$ is preferably a hydrogen atom or an alkyl group, and more preferably a hydrogen atom, a methyl group, or an ethyl group.

Examples of the substituent include a halogen, an alkyl group, an alkenyl group, an alkynyl group, an aryl group, an aralkyl group, an alkoxy group, an alkoxycarbonyl group, an alkylcarbonyloxy group, an acyl group, an alkylamino group, a carbamoyl group, a nitro group, a nitroso group, a cyano group, an alkylthio group, a sulfinyl group, a sulfonyl group, and a silyl group. In addition, among these substituents, adjacent substituents may be crosslinked to form a ring including the bonded carbon atom.

[Chem. 26]

—(Z')           (6)

Z' is halogen or OH, preferably Cl or Br.

[Chem. 27]

—(Ox)           (7)

Ox is an oxoacid selected from $NO^{3-}$, $CO_3^{2-}$, and $PO_4^{3-}$, preferably $CO_3^{2-}$.

[Chem. 28]

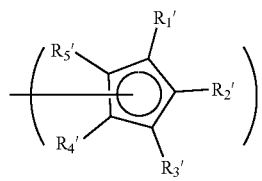
(X1)

$R_1'$, $R_2'$, $R_3'$, $R_4'$, and $R_5'$ are each independently a hydrogen atom or a hydrocarbon group which may have a substituent, preferably a hydrogen atom.

[Chem. 29]

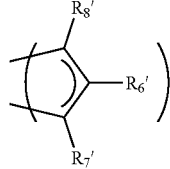
(Y1)

$R_6'$, $R_7'$, and $R_8'$ are each independently a hydrogen atom or a hydrocarbon group which may have a substituent, preferably a hydrogen atom.

In the method for producing a cyclic olefin compound according to the present embodiment, the divalent nickel complex preferably includes at least one anionic ligand Y represented by any of General Formulae (9), (11) to (13), and (Z1), and Formulae (8) and (10), and more preferably includes a carboxylate.

[Chem. 30]

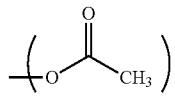
(8)

[Chem. 31]

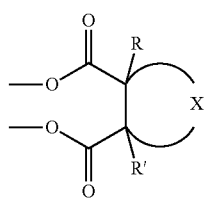
(9)

X is a group of non-metal atoms required to form a ring, and R and R' are each independently a hydrogen atom or a hydrocarbon group which may have a substituent. Examples of the hydrocarbon group include groups having 1 to 8 carbon atoms, for example, an alkyl group such as a methyl group, an ethyl group, and a propyl group; an alkenyl group such as a vinyl group and an aryl group; an alkynyl group such as an ethynyl group and a propynyl group; an allyl group such as a phenyl group and a tolyl group; and an aralkyl group such as a benzyl group and a phenethyl group. Among these, R and R' are preferably a hydrogen atom or an alkyl group, and more preferably a hydrogen atom, a methyl group, or an ethyl group.

In addition, X is a group of non-metal atoms required to constitute a ring which forms a part of $R^2$ in General Formula (3).

Examples of the substituent include a halogen, an alkyl group, an alkenyl group, an alkynyl group, an aryl group, an aralkyl group, an alkoxy group, an alkoxycarbonyl group, an alkylcarbonyloxy group, an acyl group, an alkylamino group, a carbamoyl group, a nitro group, a nitroso group, a cyano group, an alkylthio group, a sulfinyl group, a sulfonyl group, and a silyl group. In addition, among these substituents, adjacent substituents may be crosslinked to form a ring including the bonded carbon atom.

[Chem. 32]

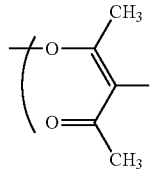
(10)

[Chem. 33]

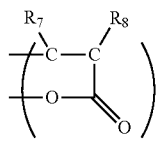
(11)

$R_7$ and $R_8$ are each independently a hydrogen atom or a hydrocarbon group which may have a substituent, and $R_7$ and $R_8$ may be bonded to each other to form a ring. Examples of the hydrocarbon group include groups having 1 to 8 carbon atoms, for example, an alkyl group such as a methyl group, an ethyl group, and a propyl group; an alkenyl group such as a vinyl group and an aryl group; an alkynyl group such as an ethynyl group and a propynyl group; an allyl group such as a phenyl group and a tolyl group; and an aralkyl group such as a benzyl group and a phenethyl group. Among these, $R_7$ and $R_8$ are preferably a hydrogen atom or an alkyl group, and more preferably a hydrogen atom, a methyl group, or an ethyl group. In addition, examples of a cyclic structure formed by bonding $R_7$ and $R_8$ to each other include 1,2-phenylene, 2,3-naphthalene, 1,2-cyclohexylene, 1,2-bicyclo[2,2,1]heptalene, and 1,4-dihydro-1,4-methano-2,3-naphthalene. Among these, 1,2-bicyclo[2,2,1]heptalene or 1,4-dihydro-1,4-methano-2,3-naphthalene is preferable.

Examples of the substituent include a halogen, an alkyl group, an alkenyl group, an alkynyl group, an aryl group, an aralkyl group, an alkoxy group, an alkoxycarbonyl group, an alkylcarbonyloxy group, an acyl group, an alkylamino group, a carbamoyl group, a nitro group, a nitroso group, a cyano group, an alkylthio group, a sulfinyl group, a sulfonyl group, and a silyl group. In addition, among these substituents, adjacent substituents may be crosslinked to form a ring including the bonded carbon atom.

[Chem. 34]

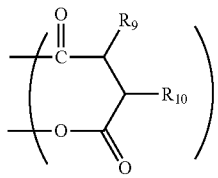

(12)

$R_9$ and $R_{10}$ are each independently a hydrogen atom or a hydrocarbon group which may have a substituent, and $R_9$ and $R_{10}$ may be bonded to each other to form a ring. Examples of the hydrocarbon group include groups having 1 to 8 carbon atoms, for example, an alkyl group such as a methyl group, an ethyl group, and a propyl group; an alkenyl group such as a vinyl group and an aryl group; an alkynyl group such as an ethynyl group and a propynyl group; an allyl group such as a phenyl group and a tolyl group; and an aralkyl group such as a benzyl group and a phenethyl group. Among these, $R_9$ and $R_{10}$ are preferably a hydrogen atom or an alkyl group, and more preferably a hydrogen atom, a methyl group, or an ethyl group.

Examples of the substituent include a halogen, an alkyl group, an alkenyl group, an alkynyl group, an aryl group, an aralkyl group, an alkoxy group, an alkoxycarbonyl group, an alkylcarbonyloxy group, an acyl group, an alkylamino group, a carbamoyl group, a nitro group, a nitroso group, a cyano group, an alkylthio group, a sulfinyl group, a sulfonyl group, and a silyl group. In addition, among these substituents, adjacent substituents may be crosslinked to form a ring including the bonded carbon atom.

[Chem. 35]

(13)

Z" is Cl or Br.

[Chem. 36]

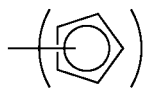

(Z1)

In the present embodiment, examples of the alicyclic dicarboxylic acid anhydride used as a raw material include a compound represented by General Formula (16), and examples of the cyclic olefin compound to be obtained include a compound represented by General Formula (17).

[Chem. 37]

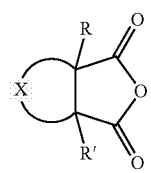

(16)

X is a group of non-metal atoms required to form a ring, and R and R' are each independently a hydrogen atom or a hydrocarbon group which may have a substituent.

[Chem. 38]

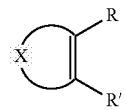

(17)

X is a group of non-metal atoms required to form a ring, and R and R' are each independently a hydrogen atom or a hydrocarbon group which may have a substituent.

X represents a group of non-metal atoms required to form a ring, and the ring composed of these may be a saturated ring or an unsaturated ring. Examples thereof include saturated rings such as cyclohexane, norbornane, bicyclo[2.2.2]octane, and tetracyclo[4.4.0.1$^{2.5}$.1$^{7.10}$]dodecane; unsaturated rings such as norbornene, tetracyclo[4.4.0.1$^{2.5}$.1$^{7.10}$]-8-dodecen, and benzonorbornene; and aprotic heterocycles such as 7-oxabicyclo[2.2.1]heptane and 7-thiabicyclo[2.2.1]heptane.

R and R' each independently represent a hydrogen atom or a hydrocarbon group which may have a substituent. Examples of the hydrocarbon group include groups having 1 to 8 carbon atoms, for example, an alkyl group such as a methyl group, an ethyl group, and a propyl group; an alkenyl group such as a vinyl group and an aryl group; an alkynyl group such as an ethynyl group and a propynyl group; an allyl group such as a phenyl group and a tolyl group; and an aralkyl group such as a benzyl group and a phenethyl group.

R and R' are preferably a hydrogen atom or an alkyl group, and more preferably a hydrogen atom, a methyl group, or an ethyl group.

R and R' may be crosslinked to each other or with a ring composed of X to form an alkylene group having 2 to 8 carbon atoms. In addition, the ring composed of X, R, and R' may have a substituent which is inert to the reaction. Examples of the substituent include a halogen, an alkyl group, an alkenyl group, an alkynyl group, an aryl group, an aralkyl group, an alkoxy group, an alkoxycarbonyl group, an alkylcarbonyloxy group, an acyl group, an alkylamino group, a carbamoyl group, a nitro group, a nitroso group, a cyano group, an alkylthio group, a sulfinyl group, a sulfonyl group, and a silyl group. In addition, among these substituents, adjacent substituents may be crosslinked to form a ring including the bonded carbon atom.

As the alicyclic dicarboxylic acid anhydride represented by General Formula (16), specifically, 5,6-benzo-2,3-dicarboxylic acid anhydrides represented by General Formula (18), a dicarboxylic acid anhydride represented by General Formula (19), or the like can be used.

[Chem. 39]

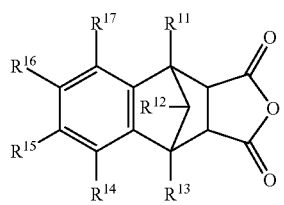

(18)

$R^{11}$, $R^{12}$, $R^{13}$, $R^{14}$, $R^{15}$, $R^{16}$, and $R^{17}$ are each independently a hydrogen atom or a substituent which may have a heteroatom.

In General Formula (18), $R^{11}$, $R^{12}$, $R^{13}$, $R^{14}$, $R^{15}$, $R^{16}$, and $R^{17}$ each independently represent a hydrogen atom or a substituent which may have a heteroatom, and it is preferable that $R^{11}$, $R^{12}$, $R^{13}$, $R^{14}$, $R^{15}$, $R^{16}$, and $R^{17}$ are all hydrogens. As the substituent, the above-described substituent can be used. In the present embodiment, a compound in which any of the substituents $R^{11}$ to $R^{17}$ is a hydrogen atom is preferable.

[Chem. 40]

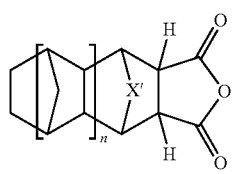

(19)

n is 0 or 1, and X' is O or $CH_2$.

As the divalent nickel complex, a commercially available product can be used as it is, but for example, the divalent nickel complex may be synthesized by a known method and used.

An amount of the divalent nickel complex used is generally 0.0001 to 0.2 mol, preferably 0.001 to 0.05 mol per 1 mol of the alicyclic dicarboxylic acid anhydride used as a raw material.

In the method for producing a cyclic olefin compound according to the present embodiment, in order to activate the nickel complex and to improve stability of the catalytic species produced, in the above-described step of producing a cyclic olefin compound, a compound which can be a ligand for the nickel complex (hereinafter, also simply referred to as a compound) may be further present.

In the method for producing a cyclic olefin compound according to the present embodiment, in order to activate the nickel complex and to improve stability of the catalytic species produced, in the above-described step of producing a cyclic olefin compound, a compound which can be a ligand for the nickel complex (hereinafter, also simply referred to as a compound) may be further present in the reaction system in the production of the cyclic olefin compound.

The compound which can be a ligand used in the present embodiment is a monodentate or polydentate electron donating compound which has, as a coordination atom, Periodic Table Group V element, that is, nitrogen, phosphorus, arsenic, or antimony. The compound which can be a ligand used in the present embodiment may be the same or different from the ligand in the nickel complex.

Examples of the compound which can be a ligand include nitrogen-containing compounds typified by tertiary amines such as tributylamine, trioctylamine, triphenylamine, N,N,N',N'-tetramethylethylenediamine, and N,N,N',N'-tetramethyl-1,2-phenylenediamine, nitrogen-containing aromatics such as 2,2'-bipyridyl and 1,10-phenanthroline, and imines such as N,N'-diphenyl-1,4-diazabutadiene and 1,6-diphenyl-2,5-diaza-1,5-hexadiene; arsenic-containing compounds such as tributylarsenic and triphenylarsenic; antimony-containing compounds such as tributylantimony and triphenylantimony; and phosphorus-containing compounds represented by General Formula (14) or General Formula (15).

Among these, the compound which can be a ligand according to the present embodiment preferably includes at least one selected from a compound represented by General Formula (14) and a compound represented by General Formula (15).

[Chem. 41]

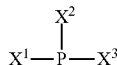

(14)

In the formula, $X^1$, $X^2$, and $X^3$ each independently represent a hydrocarbon group which may have a substituent.

[Chem. 42]

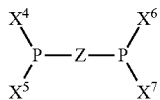

(15)

In the formula, $X^4$, $X^5$, $X^6$, and $X^7$ each independently represent a hydrocarbon group which may have a substituent. In addition, Z represents an alkylene group having 1 to 20 carbon atoms, an arylene group having 6 to 20 carbon atoms, a ferrocenylene group, or a binaphthylene group.

Examples of the hydrocarbon group in $X^1$ to $X^7$ include an alkyl group having 1 to 6 carbon atoms, an aromatic group, and a condensed ring formed by condensing a carbon ring and/or a heterocycle. In addition, examples of a substituent thereof include an alkyl group having 1 to 6 carbon atoms, an alkoxy group having 1 to 6 carbon atoms, and a halogen atom.

Examples of the compound which can be a ligand represented by General Formula (14) include trialkylphosphines such as tricyclohexylphosphine, tricyclopentylphosphine, tri-n-butylphosphine, tri-t-butylphosphine, trioctylphosphine, and tribenzylphosphine; triarylphosphines such as triphenylphosphine, tritrylphosphine (including various substituted isomers of ortho, meta, and para), tris(methoxyphenyl)phosphine (including various substituted isomers of ortho, meta, and para), tris(fluorophenyl)phosphine (including various substituted isomers of ortho, meta, and para), and tri($\alpha$-naphthyl)phosphine; diarylalkylphosphines such as diphenylcyclohexylphosphine; and dialkylarylphosphines such as dicyclohexylphenylphosphine, and triarylphosphines are preferable, and triphenylphosphine is more preferable. In addition, $X^1$, $X^2$, and $X^3$ may be crosslinked between two groups to form a ring including a phosphorus atom, and examples of such phosphine include phenylbiphenylenephosphine.

Examples of the above-described compound which can be a ligand represented by General Formula (15) include 1,2-bis(diphenylphosphino)ethane, 1,3-bis(diphenylphosphino)propane, and 1,4-bis(diphenylphosphino)butane.

In the present embodiment, from the viewpoint of obtaining a high-purity target substance with high selectivity, it is preferable to use a compound which can be a ligand represented by General Formula (14) or (15).

In the present embodiment, in order to improve stability of the nickel complex, it is preferable that the compound which can be a ligand is coexisted in large excess. In a case where the amount of the compound which can be a ligand is too small, the stability of the catalyst may decrease. On the other hand, in a case where the amount of the ligand is large, the stability of the catalyst may not improve in proportion to the amount used, which may be uneconomical or the reaction rate may decrease.

Therefore, in the step of producing a cyclic olefin compound according to the present embodiment, the amount of the compound which can be a ligand used is not always constant depending on the type thereof, but for example, the amount thereof is 10 to 500 mol, preferably 20 to 200 mol per 1 mol of the nickel complex.

By using the compound which can be a ligand in the above-described amount, a high-purity cyclic olefin can be produced with a high selectivity. Further, as long as it is within this range, this compound itself may be used as a solvent. In this case, the compound used is preferably a compound which is stable with respect to the target compound and is relatively inexpensive. Among these, triphenylphosphine is one of the useful compounds.

These compounds which can be a ligand may be used alone, or may be used as a mixture of two or more kinds thereof. In a case where a mixture of these compounds which can be a ligand is used, these compounds may be mixed at any proportion, but it is preferable that the total amount of these compounds used is within the above-described range with respect to 1 mol of the nickel complex.

A higher reaction temperature is advantageous in terms of reaction rate, but in a case of being too high, it may cause adverse side reactions such as catalyst decomposition, rearrangement or polymerization of the cyclic olefin product, resulting in a decrease in selectivity. Therefore, it is usually preferable to carry out the reaction at 100° C. to 300° C., particularly 150° C. to 250° C.

In the method for producing a cyclic olefin compound according to the present embodiment, in order to suppress deactivation of the nickel complex and to increase the selectivity by reducing thermal history of the cyclic olefin compound produced, in the step of producing a cyclic olefin compound, it is preferable to remove the generated cyclic olefin compound to an outside of a reaction system. Therefore, it is desirable to adopt a reactive distillation method.

A reaction pressure largely depends on a boiling point of the olefin produced, but is not particularly limited as long as rapid removal of the product to the outside of the reaction system is achieved. In a case where the boiling point of the product is low, the reaction can be carried out at normal pressure. On the other hand, in a case where the boiling point of the product is high, it is preferable to carry out the reaction under reduced pressure.

The cyclic olefin compound represented by General Formula (17), which is obtained from the alicyclic dicarboxylic acid anhydride of General Formula (16), is taken out in a form of a gas and then separated from the gas including CO and $CO_2$ by condensation. The crude cyclic olefin compound thus obtained may be further purified by distillation or the like as necessary.

In the reaction, in a case where the compound which can be a ligand itself can play a role of a solvent, the reaction may be carried out without using any other solvent, but another solvent may be used as necessary.

As the solvent, any solvent can be used as long as it is a solvent which is inert to the raw material, the catalyst, and the compound which can be a ligand. Examples thereof include ethers such as diethylene glycol dimethyl ether, triethylene glycol dimethyl ether, tetraethylene glycol dimethyl ether, diphenyl ether, anisole, and veratrole; aromatic hydrocarbons such as tetralin and naphthalene; and aprotic polar solvents such as nitrobenzene, benzonitrile, N-methylpyrrolidone, and dimethylimidazolidinone.

The solvents (or the compound which can be a ligand) are preferably one which can be easily separated from the cyclic olefin product, and generally, one having a boiling point higher than that of the cyclic olefin product are used. In a case where such solvents as described above are used, it is possible to suppress evaporation of the solvents (or the compound which can be a ligand) from the reaction mixture, in which the catalyst and the compound which can be a ligand, are dissolved, while separating the product including the target cyclic olefin from the reaction mixture by reactive distillation, and therefore such solvents are also advantageous in that it is not necessary to newly supply these solvents (or compounds which can be a ligand), and complicated separation and purification of the product mixture can be avoided.

The reaction is preferably carried out under the conditions in which oxygen and water are removed, and is usually carried out in an inert atmosphere such as nitrogen or argon.

The reaction can be carried out by either a batch process or a continuous process in which the nickel complex, the compound which can be a ligand, the dicarboxylic acid anhydride as a raw material, and the solvent are continuously supplied to a reactor.

In addition, the reaction can be carried out by a batch process, a continuous process in which the nickel complex, the compound which can be a ligand, the dicarboxylic acid anhydride as a raw material, and the solvent are continuously supplied to a reactor, or a semi-batch process combining these methods, but it is preferable to carry out by a semi-batch method. As a result, since the time required to start the reaction (reaction induction period) can be shortened, and also the residence time of the raw material and the product can be shortened, and thereby the generation of by-products can be suppressed by shortening the thermal history.

Further, as will be described later, in a case where the compound which can be a ligand is present with the nickel complex in the step of producing a cyclic olefin compound, by carrying out the reaction by a semi-batch process in which the raw material and the nickel complex are continuously supplied to the reaction vessel charged in advance with the compound which can be a ligand, the yield of the cyclic olefin compound per the compound which can be a ligand can be improved.

In the method for producing a cyclic olefin compound according to the present embodiment, a step of adding an alcohol compound can be included. As a result, it is possible to detoxify impurities generated during the production of the alicyclic dicarboxylic acid anhydride. The impurities in the alicyclic dicarboxylic acid anhydride inhibits the activation of the divalent nickel complex, and the time required to start the reaction (reaction induction period) becomes longer. Therefore, by adding an alcohol compound to detoxify the impurities included in the alicyclic dicarboxylic acid anhydride, the reaction induction period can be shortened, and the production rate of the cyclic olefin compound can be improved.

Here, the step of adding an alcohol compound may be performed separately from the step of producing a cyclic olefin compound, or may be performed at the same time as the step of producing a cyclic olefin compound. That is, after treating the alicyclic dicarboxylic acid anhydride including impurities with an alcohol compound, the alicyclic dicarboxylic acid anhydride is mixed with the divalent nickel complex and the compound which can be a ligand, and then the step of producing a cyclic olefin compound may be performed. Alternatively, an alcohol compound may be further added in a case of mixing the alicyclic dicarboxylic acid anhydride including impurities, the divalent nickel complex, and the compound which can be a ligand. In this case, the order in which the alicyclic dicarboxylic acid anhydride including impurities, the divalent nickel complex, the compound which can be a ligand, and the alcohol compound are added is not particularly limited. However, it is preferable that the alcohol compound is added before the decarbonylation or decarboxylation reaction of the alicyclic dicarboxylic acid anhydride begins, and the alcohol compound is removed before the decarbonylation or decarboxylation reaction of the alicyclic dicarboxylic acid anhydride begins.

In the method for producing a cyclic olefin compound according to the present embodiment, it is preferable that a boiling point of the alcohol compound is lower than a boiling point of the alicyclic dicarboxylic acid anhydride. As a result, after the detoxification of the impurities is completed, the alcohol compound can be selectively removed from the system before the synthesis of the cyclic olefin compound.

In a case where the produced cyclic olefin compound is benzonorbornadiene, as the alcohol compound, for example, it is preferable to include one or two or more kinds selected from 1-butanol, 3-pentanol, 2-methoxyethanol, isoamyl alcohol, 1-pentanol, 1-hexanol, cyclohexanol, 1-octanol, 1-nonanol, 1-decanol, 1-undecanol, and 1-dodecanol.

In the method for producing a cyclic olefin compound according to the present embodiment, the alicyclic dicarboxylic acid anhydride may include, for example, at least one of a carboxylic acid compound or a carboxylic acid anhydride (excluding the alicyclic dicarboxylic acid anhydride) as an impurity.

Depending on the type of the divalent nickel complex, these impurities may inhibit the activation of the divalent nickel complex. In the method for producing a cyclic olefin compound according to the present embodiment, in a case that it further includes the step of adding an alcohol compound, the carboxylic acid compound or acid anhydride in the impurities reacts with the alcohol compound to be detoxified.

In the method for producing a cyclic olefin compound according to the present embodiment, the above-described step of adding an alcohol compound preferably includes a step of contacting the alcohol compound with the impurity in a liquid phase to react the alcohol compound with the carboxylic acid compound or the carboxylic acid anhydride in the impurity, and removing an unreacted alcohol compound.

As a result, the inhibition of the synthetic reaction of the cyclic olefin compound by alcohol is suppressed, so that the production rate of the cyclic olefin compound can be improved.

EXAMPLE

Hereinafter, usefulness of the present invention will be described in more detail with Examples, but the present invention is not limited thereto. The analysis was performed by gas chromatography, the conversion rate and selectivity were determined by the internal standard method (mol %), and the purity was determined by the area percentage (%). In addition, the concentrations of carbon monoxide and carbon dioxide generated were measured using an infrared gas concentration analyzer, CGT-7000 manufactured by Shimadzu Corporation.

Synthesis Example 1

Synthesis of Benzonorbornene-2,3-Dicarboxylic Acid anhydride (BNDCA)

380.1 g (3.14 mol) of indene (manufactured by JFE Chemical Corporation, purity: 96%), 282.9 g (2.88 mol) of maleic anhydride, 5.69 g (28.6 mmol) of phenothiazine, and 501.5 g of methyl isobutyl ketone were charged into a 1.5 L SUS316 autoclave, and the reaction solution was stirred at 220° C. for 4 hours. After cooling the reaction mixture to room temperature, the precipitated solid was separated by suction filtration, washed with methyl isobutyl ketone, and dried (424.0 g). As a result of analyses by mass spectrometry and NMR of the solid substance, the product was identified as benzonorbornene-2,3-dicarboxylic acid anhydride (EI m/z 214 ($M^+$)). As a result of analysis by gas chromatography, the purity was equal to or more than 99% (isolation yield 69% based on maleic anhydride).

The obtained compound was used in Synthesis Example 4.

Synthesis Example 2

Synthesis of [(tmeda)Ni($C_2H_4$COO)](N,N'-Tetramethylethylenediamine Nickelacyclopropionate)

(Reference: Z. anorg. allg. Chem., 1989, 577, 111 to 114)
Finely crushed succinic anhydride (0.207 g) was weighed into a dried 50 mL flask. To the flask, bis(1,5-cyclooctadiene) nickel (0.854 g) was added in a glove box under a nitrogen atmosphere, and then dried tetramethylethylenediamine (tmeda, 2.077 g) was added. The resulting yellow slurry was stirred overnight at room temperature to obtain a lime green slurry. The slurry was filtered under nitrogen and the remaining solid was dissolved in dry methanol. The solution was further filtered under nitrogen and washed with dry methanol. The obtained filtrate was concentrated, and the precipitated solid was recovered (0.4 g, yield: 78%). $^1$H NMR (CD$_3$OD, 25° C.): δ 0.46 (br, 2H, Ni—CH$_2$), 1.83 (br, 2H, CH$_2$COO), 2.26 to 2.52 (m, 4H+6H+6H, NCH$_2$CH$_2$N+ N(CH$_3$)$_2$+N(CH$_3$)$_2$) ppm (tmeda)Ni(C$_2$H$_4$COO) is represented by Formula (A).

[Chem. 43]

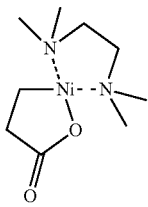

(A)

Synthesis Example 3

Synthesis of [(dppe)Ni(C$_2$H$_4$COO)] (dppe: Ph$_2$P(CH$_2$)$_2$PPh$_2$; Ph is phenyl Group)

dppe (1.03 g) was added to the crude product (0.835 g) of [(tmeda)Ni(C$_2$H$_4$COO)] synthesized in the same manner as in Synthesis Example 2, and 30 mL of dry THF was further added thereto to obtain a dark green slurry. A yellow slurry obtained by further stirring at room temperature for 4 hours was filtered under nitrogen and dried to obtain a yellow solid (1.23 g, yield: 69%). $^1$H NMR (CD$_2$Cl$_2$, 25° C.): δ 0.82 (m, 2H, Ni—CH$_2$), 2.03 to 2.36 (m, 2H+2H+4H, P—CH$_2$+P—CH$_2$+CH$_2$COO), 7.47 to 7.87 (m, 20H, 4Ph) ppm (dppe)Ni(C$_2$H$_4$COO) is represented by Formula (B).

[Chem. 44]

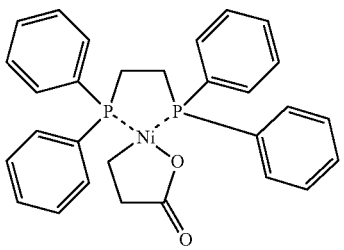

(B)

Synthesis Example 4

Synthesis of nickel benzonorbornene-2,3-dicarboxylate (BNDCA-Ni)

3.20 g (80 mmol) of sodium hydroxide and 80 ml of water were charged into a 200 ml three-necked flask and dissolved. To the flask, 8.57 g (40 mmol) of benzonorbornene-2,3-dicarboxylic acid anhydride (BNDCA) was charged in one portion, and the mixture was stirred at 80° C. After confirming the dissolution of BNDCA, 9.51 g (40 mmol) of nickel chloride hexahydrate dissolved in 20 ml of water was charged thereto using a dropping funnel, and the reaction solution was stirred at 80° C. for 1 and a half hours. After cooling the reaction solution to room temperature, the precipitated solid was separated by suction filtration, washed with water and acetone, and dried to obtain a green solid (9.91 g, yield: 86%). Nickel benzonorbornene-2,3-dicarboxylate (BNDCA-Ni) is represented by Formula (C).

[Chem. 45]

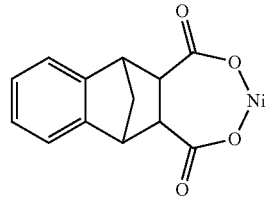

(C)

Example 1

9.97 g of benzonorbornene-2,3-dicarboxylic acid anhydride (BNDCA), 5.10 g of triphenylphosphine, and 0.097 g of nickel acetate tetrahydrate (Ni(OAc)$_2$.4H$_2$O) were charged into a 50 mL glass flask equipped with a distillation apparatus, and the respective components were mixed and heated to 223° C. under reduced pressure of 30 torr.

If the reaction is considered to start when the temperature reached 223° C., the distilling of the liquid started after 50 minutes after of the start of the reaction, and the distilling of the liquid almost subsided 5.5 hours later. The distillate was confirmed to be benzonorbornadiene as a result of analysis by $^1$H NMR. The yield of benzonorbornadiene was 85.1%, the selectivity was 99.7%, and the purity was 99.3%. In addition, the molar ratio of benzonorbornadiene and triphenylphosphine was 1.94.

The molar ratio of benzonorbornadiene and triphenylphosphine indicates the molar ratio of benzonorbornadiene obtained with respect to 1 mol of triphenylphosphine charged. As the value is larger, the yield of benzonorbornadiene per triphenylphosphine is higher.

Example 2

Using the same equipment as in Example 1, 10.20 g of BNDCA, 5.20 g of triphenylphosphine, and 0.114 g of nickel benzonorbornene-2,3-dicarboxylate (BNDCA-Ni) were charged, and the same operation as in Example 1 was carried out, except that the reaction temperature was changed to 228° C. The yield of benzonorbornadiene was 67.6%, the selectivity was 99.4%, and the purity was 98.4%. As the above-described nickel benzonorbornene-2,3-dicarboxylate (BNDCA-Ni), the compound obtained in Synthesis Example 4, which is represented by Formula (C), was used.

[Chem. 46]

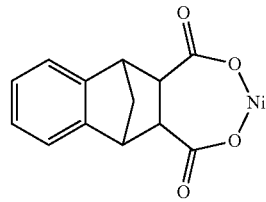

(C)

Example 3

Using the same equipment as in Example 1, 10.28 g of BNDCA, 5.33 g of triphenylphosphine, and 0.0984 g of the nickel complex obtained in Synthesis Example 2 were charged, and the same operation as in Example 1 was carried out. The yield of benzonorbornadiene was 21.5%.

Example 4

Using the same equipment as in Example 1, 10.15 g of BNDCA, 5.18 g of triphenylphosphine, and 0.2103 g of the nickel complex obtained in Synthesis Example 3 were charged, and the same operation as in Example 1 was carried out, except that the reaction temperature was changed to 218° C. The yield of benzonorbornadiene was 49.3%, the selectivity was 99.7%, and the purity was 98.1%.

Example 5

The same operation as in Example 4 was carried out, except that, in Example 4, the reaction temperature was changed to 228° C. The yield of benzonorbornadiene was 59.6%, the selectivity was 99.6%, and the purity was 98.0%.

Example 6

Using the same equipment as in Example 1, 10.36 g of BNDCA, 5.28 g of triphenylphosphine, and 0.106 g of nickel (II) acetylacetonate (Ni(acac)$_2$) were charged, and the same operation as in Example 1 was carried out, except that the reaction temperature was changed to 228° C. The yield of benzonorbornadiene was 79.0%, the selectivity was 99.6%, and the purity was 99.3%.

Example 7

The same operation as in Example 1 was carried out, except that, in Example 1, 0.097 g of nickel acetate tetrahydrate was changed to 0.0956 g of nickel chloride hexahydrate (NiCl$_2$·6H$_2$O), and the reaction temperature was changed to 220° C.
The yield of benzonorbornadiene was 40.3%, the selectivity was 96.4%, and the purity was 95.1%.

Example 8

The respective components were mixed in the same manner as in Example 1, except that 0.097 g of nickel acetate tetrahydrate in Example 1 was changed to 0.088 g of nickel bromide (NiBr$_2$). After raising the temperature to 220° C. under reduced pressure of 30 torr, the reaction was carried out for 150 minutes while gradually raising the temperature to 235° C. The yield of benzonorbornadiene was 28.2%, the selectivity was 98.3%, and the purity was 96.5%.

Example 9

The same operation as in Example 1 was carried out, except that 0.097 g of nickel acetate tetrahydrate in Example 1 was changed to 0.0628 g of nickelocene (Cp$_2$Ni), and the reaction temperature was changed to 220° C. The yield of benzonorbornadiene was 74.9%, the selectivity was 99.5%, and the purity was 98.4%.

Example 10

The respective components were mixed in the same manner as in Example 1, except that 0.097 g of nickel acetate tetrahydrate in Example 1 was changed to 0.0819 g of nickel carbonate (NiCO$_3$). After reacting at 220° C. for 160 minutes under reduced pressure of 30 torr, the reaction was carried out for 8 hours while gradually raising the temperature to 235° C. The yield of benzonorbornadiene was 26.5%, the selectivity was 99.8%, and the purity was 96.1%.

Example 11

The same operation as in Example 1 was carried out, except that 0.097 g of nickel acetate tetrahydrate in Example 1 was changed to 0.074 g of nickel formate dihydrate (Ni(OCOH)$_2$·2H$_2$O), and the reaction temperature was changed to 228° C.
After reacting at 228° C. for 70 minutes, the reaction was further carried out for 100 minutes while raising the temperature to 237° C. The yield of benzonorbornadiene was 62.8%, the selectivity was 99.8%, and the purity was 98.5%.

Example 12

The same operation as in Example 1 was carried out, except that 0.142 g of 1-hexanol was further charged in addition to benzonorbornene-2,3-dicarboxylic acid anhydride, triphenylphosphine, and nickel acetate tetrahydrate. CO and CO$_2$ gas was generated immediately before the reaction temperature reached 220° C., and the distilling of the liquid started immediately after reaching 220° C. and the distilling of the liquid almost subsided 280 minutes later. The yield of benzonorbornadiene was 68.4%, the selectivity was 99.5%, and the purity was 99.2%. Table 2 shows the presence or absence of addition of 1-hexanol and the time (induction period (minutes)) from reaching the reaction temperature (220° C.) to the generation of CO and CO$_2$ gas. The molar ratio of benzonorbornadiene and triphenylphosphine was 1.64.

Example 13

9.97 g of benzonorbornene-2,3-dicarboxylic acid anhydride, 5.06 g of triphenylphosphine, and 0.135 g of 1-hexanol were charged into a 50 mL glass flask equipped with a distillation apparatus, and the mixture was heated to 220° C. for 5 minutes under reduced pressure of 30 torr. After cooling to approximately 60° C., the pressure was returned to normal with nitrogen, and 0.096 g of nickel acetate tetrahydrate was added thereto. When the mixture was heated to 220° C. under reduced pressure of 30 torr again, CO and CO$_2$ gas was generated immediately before the reaction temperature reached 220° C., and the distilling of the liquid started 10 minutes later and the distilling of the liquid almost subsided 3.5 hours later. The yield of benzonorbornadiene was 87.9%, the selectivity was 99.7%, and the purity was 98.3%. Table 2 shows the presence or absence of addition of 1-hexanol and the time (induction period (minutes)) from reaching the reaction temperature (220° C.) to the generation of CO and CO$_2$ gas. The molar ratio of benzonorbornadiene and triphenylphosphine was 2.12.

Example 14

10.01 g of benzonorbornene-2,3-dicarboxylic acid anhydride, 5.13 g of triphenylphosphine, and 0.072 g of 1-hexanol were charged into a 50 mL glass flask equipped with a distillation apparatus and a dropping funnel. To another flask, 0.157 g of nickel acetate tetrahydrate and 2.27 g of tetraethylene glycol dimethyl ether were added. The resulting slurry was exposed to air with stirring. The reactor was heated to 220° C. under reduced pressure of 30 torr, and the nickel slurry exposed to air was added thereto from the dropping funnel in small portions over 280 minutes. The distilling of the liquid started 20 minutes after the first slurry addition, and the distilling thereof almost subsided after 280 minutes. Among distillates, benzonorbornadiene was 5.84 g, and tetraethylene glycol dimethyl ether was 1.09 g. The yield of benzonorbornadiene in this reaction was 96.9%, the selectivity was 99.8%, and the purity excluding tetraethylene glycol dimethyl ether was 94.0%. The molar ratio of benzonorbornadiene and triphenylphosphine was 2.32.

Example 15

18.33 g of benzonorbornene-2,3-dicarboxylic acid anhydride (BNDCA), 3.97 g of triphenylphosphine, and 0.353 g of nickel acetate tetrahydrate ($Ni(OAc)_2 \cdot 4H_2O$) were charged into a 50 mL glass flask equipped with a distillation apparatus, and the respective components were mixed and heated to 220° C. under reduced pressure of 30 torr.

If the reaction is considered to start when the temperature reached 220° C., the distilling of the liquid started after 90 minutes of the start of the reaction, and the distilling of the liquid almost subsided 3 hours later. The distillate was confirmed to be benzonorbornadiene as a result of analysis by 1H NMR. The yield of benzonorbornadiene was 77.0%, the selectivity was 99.9%, and the purity was 92.2%. The molar ratio of benzonorbornadiene and triphenylphosphine was 4.3. The results are shown in Table 3.

Example 16

4.34 g of triphenylphosphine was charged into a 50 mL glass flask (1) equipped with a distillation apparatus and a dropping funnel with a pressure equalizing tube which could be opened and closed by a valve. 22.24 g of benzonorbornene-2,3-dicarboxylic acid anhydride (BNDCA), 0.323 g of nickel acetate tetrahydrate ($Ni(OAc)_2 \cdot 4H_2O$), and 29.43 g of tetraethylene glycol dimethyl ether were charged into another two-necked flask (2) under nitrogen to obtain a slurry. The flask (1) was heated to 220° C. by an oil bath under reduced pressure of 30 torr.

Thereafter, (a) the slurry of the flask (2) was withdrawn with a syringe in a fixed amount (approximately 2 g) under stirring, charged into the dropping funnel, and the weight thereof was precisely weighed from the weight of the syringe before and after charging, and then (i) the pressure equalizing tube valve of the dropping funnel was slowly opened to bring the pressure to the same level as that of the reactor, and then the slurry was charged into the reactor (start of reaction). The operations of (a) and (i) were repeated 22 times every 20 minutes. Immediately after the start of the reaction, gas generation and liquid distillation were observed.

After 460 minutes, 41 mL of liquid distillate was obtained. This liquid was a tetraethylene glycol dimethyl ether solution of benzonorbornadiene, and the yield of benzonorbornadiene was 97.9%, the selectivity was 99.9%, and the purity excluding tetraethylene glycol dimethyl ether was 96.4%. The molar ratio of benzonorbornadiene and triphenylphosphine was 5.9. The results are shown in Table 3.

Example 17

The same operation as in Example 16 was carried out, except that the amounts of triphenylphosphine, benzonorbornene-2,3-dicarboxylic acid anhydride (BNDCA), nickel acetate tetrahydrate ($Ni(OAc)_2 \cdot 4H_2O$), and tetraethylene glycol dimethyl ether in Example 16 were changed to 4.33 g, 21.57 g, 0.209 g, and 27.24 g, respectively.

After 480 minutes, 40 mL of liquid distillate was obtained. This liquid was a tetraethylene glycol dimethyl ether solution of benzonorbornadiene, and the yield of benzonorbornadiene was 96.0%, the selectivity was 99.8%, and the purity excluding tetraethylene glycol dimethyl ether was 96.7%. The molar ratio of benzonorbornadiene and triphenylphosphine was 5.6. The results are shown in Table 3.

Example 18

3.54 g of triphenylphosphine was charged into a 50 mL glass flask (1) equipped with a distillation apparatus and two dropping funnels with a pressure equalizing tube which could be opened and closed by a valve, and one of the dropping funnels was covered with a rubber heater and kept at 180° C. 27.00 g of benzonorbornene-2,3-dicarboxylic acid anhydride (BNDCA) and 44.07 g of tetraethylene glycol dimethyl ether were charged into another two-necked flask (2) under nitrogen to obtain a slurry. 0.424 g of nickel acetate tetrahydrate ($Ni(OAc)_2 \cdot 4H_2O$) and 10.20 g of tetraethylene glycol dimethyl ether were charged into another Schlenk tube to obtain a slurry. The flask (1) was heated to 220° C. by an oil bath under reduced pressure of 30 torr.

(a) The slurry of the flask (2) was withdrawn with a syringe in a fixed amount (approximately 2.5 g) under stirring, charged into the dropping funnel kept at 180° C., and the weight thereof was precisely weighed from the weight of the syringe before and after charging.

(i) The slurry of the Schlenk tube was withdrawn with a syringe in a fixed amount (approximately 2.5 g) under stirring, charged into the other dropping funnel, and the weight thereof was precisely weighed from the weight of the syringe before and after charging.

(u) The solution of (a) and the slurry of (i) were charged into the reactor by the same operation as in Example 16 every 20 minutes over 500 minutes.

As a result, immediately after the start of the reaction, gas generation and liquid distillation were observed, and finally 54 mL of liquid was distilled. This liquid was a tetraethylene glycol dimethyl ether solution of benzonorbornadiene, and the yield of benzonorbornadiene was 86.8%, the selectivity was 99.9%, the purity excluding tetraethylene glycol dimethyl ether was 95.2%, and the molar ratio of benzonorbornadiene and triphenylphosphine was 7.3. The results are shown in Table 3.

In Examples 16 to 18, the yield of benzonorbornadiene per triphenylphosphine could be improved while maintaining a high yield without an induction period.

Comparative Example 1

The same operation as in Example 1 was carried out, except that, in Example 1, 0.097 g of nickel acetate tetrahydrate was changed to 0.100 g of nickel sulfate hexahydrate ($NiSO_4 \cdot 6H_2O$), and the reaction temperature was changed to 228° C. The temperature was gradually raised to 240° C., but no liquid distillate was obtained.

Comparative Example 2

The same operation as in Example 1 was carried out, except that, in Example 1, 0.097 g of nickel acetate tetrahydrate was changed to 0.03 g of nickel oxide (NiO), and the reaction temperature was changed to 222° C. The temperature was gradually raised to 237° C., but no liquid distillate was obtained.

TABLE 1

| Nickel complex | Temperature (° C.) | Yield (%) | Selectivity (%) |
|---|---|---|---|
| Example 1 | Ni(OAc)$_2$•4H$_2$O | 223 | 85.1 | 99.7 |
| Example 2 | BNDCA-Ni | 228 | 67.6 | 99.4 |
| Example 3 | (tmeda)Ni(C$_2$H$_4$COO) | 223 | 21.5 | n.d. |
| Example 4 | (dppe)Ni(C$_2$H$_4$COO) | 218 | 49.3 | 99.7 |
| Example 5 | (dppe)Ni(C$_2$H$_4$COO) | 228 | 59.6 | 99.6 |
| Example 6 | Ni(acac)$_2$ | 228 | 79.0 | 99.6 |
| Example 7 | NiCl$_2$•6H$_2$O | 220 | 40.3 | 96.4 |
| Example 8 | NiBr$_2$ | 220 to 235 | 28.2 | 98.3 |
| Example 9 | Cp$_2$Ni | 220 | 74.9 | 99.5 |
| Example 10 | NiCO$_3$ | 220 to 235 | 26.5 | 99.8 |
| Example 11 | Ni(OCOH)$_2$•2H$_2$O | 228 to 237 | 62.8 | 99.8 |
| Example 12 | Ni(OAc)$_2$•4H$_2$O | 220 | 68.4 | 99.5 |
| Example 13 | Ni(OAc)$_2$•4H$_2$O | 220 | 87.9 | 99.7 |
| Example 14 | Ni(OAc)$_2$•4H$_2$O | 220 | 96.9 | 99.8 |
| Comparative Example 1 | NiSO$_4$•6H$_2$O | 228 to 240 | 0 | — |
| Comparative Example 2 | NiO | 222 to 237 | 0 | — |

TABLE 2

| Example | 1-Hexanol addition | Induction period[1] (minute) |
|---|---|---|
| 1 | None | 50 |
| 12 | Yes | 0 |
| 13 | Yes | 0 |

[1]time from reaching the reaction temperature (220° C.) to the generation of CO and CO$_2$ gas

TABLE 3

| | Nickel complex | Temperature (° C.) | Yield (%) | Selectivity (%) | Molar ratio of benzonorbornadiene and triphenylphosphine |
|---|---|---|---|---|---|
| Example 15 | Ni(OAc)$_2$•4H$_2$O | 220 | 77.0 | 99.9 | 4.3 |
| Example 16 | Ni(OAc)$_2$•4H$_2$O | 220 | 97.9 | 99.9 | 5.9 |
| Example 17 | Ni(OAc)$_2$•4H$_2$O | 220 | 96.0 | 99.8 | 5.6 |
| Example 18 | Ni(OAc)$_2$•4H$_2$O | 220 | 86.8 | 99.9 | 7.3 |

Hereinafter, examples of the reference form will be added.

[1]

A method for producing a cyclic olefin compound, including:

a step of producing a cyclic olefin compound by acting a divalent nickel complex represented by General Formula (1) to decarbonylate and decarboxylate an alicyclic dicarboxylic acid anhydride, in which the divalent nickel complex includes at least one anionic ligand Y represented by any of General Formulae (2) to (7), (X), and (Y), $$\text{Ni(Y)}_m\text{(L)}_n \quad (1)$$

(here, Ni is divalent nickel, Y is an anionic monodentate or polydentate ligand and has at least one Ni-E covalent bond, E is a heteroatom or a π-bonding group, m is 1 or 2, L is a neutral ligand, and n is a real number of 0 to 6)

[Chem. 47]

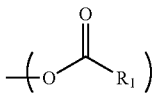

(2)

($R_1$ is a hydrogen atom or a hydrocarbon group which may have a substituent)

[Chem. 48]

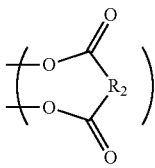

(3)

($R_2$ is a divalent hydrocarbon group which may have a substituent)

[Chem. 49]

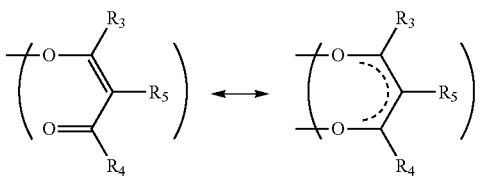

(4)

($R_3$, $R_4$, and $R_5$ are hydrocarbon groups which may have a substituent, and $R_3$ and $R_5$ or $R_4$ and $R_5$ may be bonded to each other to form a ring)

[Chem. 50]

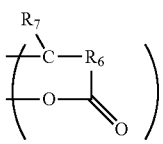

(5)

($R_6$ is a divalent hydrocarbon group which may have a substituent, $R_7$ is a hydrogen atom, a hydrocarbon group which may have a substituent, or an oxo group, and in a case where $R_7$ is a hydrocarbon group, $R_7$ may be bonded to $R_6$ to form a ring)

[Chem. 51]

—(Z')     (6)

(Z' is halogen or OH)

[Chem. 52]

—(Ox)     (7)

(Ox is an oxoacid selected from $NO^{3-}$, $CO_3^{2-}$, and $PO_4^{3-}$)

[Chem. 53]

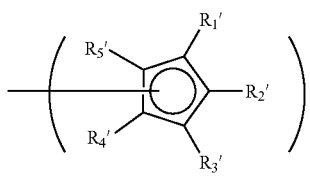
(X)

($R_1'$, $R_2'$, $R_3'$, $R_4'$, and $R_5'$ are each independently a hydrogen atom or a hydrocarbon group which may have a substituent)

[Chem. 54]

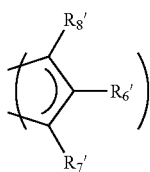
(Y)

($R_6'$, $R_7'$, and $R_8'$ are each independently a hydrogen atom or a hydrocarbon group which may have a substituent).

[2]

The method for producing a cyclic olefin compound according to [1],
in which the divalent nickel complex includes at least one anionic ligand Y represented by any of General Formulae (8) to (13) and (Z),

[Chem. 55]

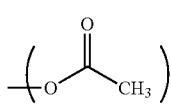
(8)

[Chem. 56]

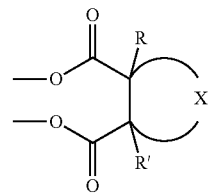
(9)

(X is a group of non-metal atoms required to form a ring, and R and R' are each independently a hydrogen atom or a hydrocarbon group which may have a substituent)

[Chem. 57]

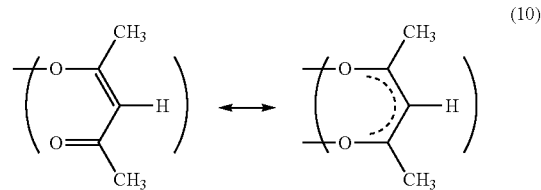
(10)

[Chem. 58]

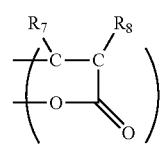
(11)

($R_7$ and $R_8$ are each independently a hydrogen atom or a hydrocarbon group which may have a substituent, and $R_7$ and $R_8$ may be bonded to each other to form a ring)

[Chem. 59]

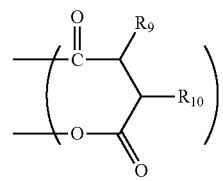
(12)

($R_9$ and $R_{10}$ are each independently a hydrogen atom or a hydrocarbon group which may have a substituent, and $R_9$ and $R_{10}$ may be bonded to each other to form a ring)

[Chem. 61]

—(Z")     (13)

(Z" is Cl or Br)

[Chem. 61]

(Z)

[3]

The method for producing a cyclic olefin compound according to [1] or [2],
  in which, in the step of producing a cyclic olefin compound, a compound which can be a ligand for the nickel complex is further present.

[4]

The method for producing a cyclic olefin compound according to [3],
  in which, in the step of producing a cyclic olefin compound, the compound which can be a ligand is present in an amount of 10 to 500 mol with respect to 1 mol of the nickel complex.

[5]

The method for producing a cyclic olefin compound according to [3] or [4],
  in which the compound which can be a ligand includes a phosphorus-containing compound.

[6]

The method for producing a cyclic olefin compound according to any one of [3] to [5],
  in which the compound which can be a ligand includes at least one selected from a compound represented by General Formula (14) and a compound represented by General Formula (15),

[Chem. 62]

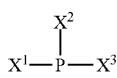
(14)

($X^1$, $X^2$, and $X^3$ are each independently a hydrocarbon group which may have a substituent)

[Chem. 63]

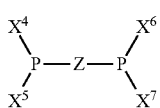
(15)

($X^4$, $X^5$, $X^6$, and $X^7$ are each independently a hydrocarbon group which may have a substituent, and Z is an alkylene group having 1 to 20 carbon atoms, an arylene group having 6 to 20 carbon atoms, a ferrocenylene group, or a binaphthylene group)

[7]

The method for producing a cyclic olefin compound according to any one of [3] to [6],
  in which the compound which can be a ligand includes triphenylphosphine.

[8]

The method for producing a cyclic olefin compound according to any one of [1] to [7], further including:
  a step of adding an alcohol compound.

[9]

The method for producing a cyclic olefin compound according to [8],
  in which a boiling point of the alcohol compound is lower than a boiling point of the alicyclic dicarboxylic acid anhydride.

[10]

The method for producing a cyclic olefin compound according to any one of [1] to [9],
  in which the alicyclic dicarboxylic acid anhydride includes at least one of a carboxylic acid compound or a carboxylic acid anhydride (excluding the alicyclic dicarboxylic acid anhydride) as an impurity.

[11]

The method for producing a cyclic olefin compound according to [10], further including:
  a step of contacting the alcohol compound with the impurity in a liquid phase to react the alcohol compound with the carboxylic acid compound or the carboxylic acid anhydride in the impurity, and removing an unreacted alcohol compound.

[12]

The method for producing a cyclic olefin compound according to any one of [1] to [11],
  in which the alicyclic dicarboxylic acid anhydride includes a compound represented by General Formula (16), and
  the cyclic olefin compound includes a compound represented by General Formula (17),

[Chem. 64]

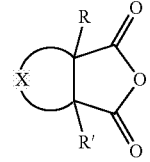
(16)

(X is a group of non-metal atoms required to form a ring, and R and R' are each independently a hydrogen atom or a hydrocarbon group which may have a substituent)

[Chem. 65]

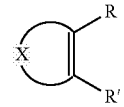
(17)

(X is a group of non-metal atoms required to form a ring, and R and R' are each independently a hydrogen atom or a hydrocarbon group which may have a substituent)

[13]

The method for producing a cyclic olefin compound according to any one of [1] to [12],
  in which the alicyclic dicarboxylic acid anhydride includes 5,6-benzo-2,3-dicarboxylic acid anhydrides represented by General Formula (18),

[Chem. 66]

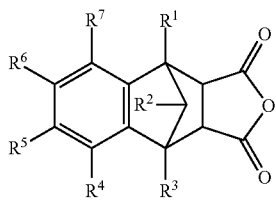

(18)

(R¹, R², R³, R⁴, R⁵, R⁶, and R⁷ are each independently a hydrogen atom or a substituent which may have a heteroatom)

[14] The method for producing a cyclic olefin compound according to [13],
in which R¹, R², R³, R⁴, R⁵, R⁶, and R⁷ in General Formula (18) are all hydrogens.

[15] The method for producing a cyclic olefin compound according to any one of [1] to [14],
in which the alicyclic dicarboxylic acid anhydride includes a dicarboxylic acid anhydride represented by General Formula (19),

[Chem. 67]

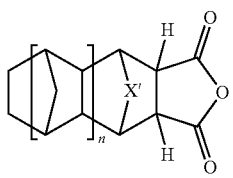

(19)

(n is 0 or 1, and X' is O or CH₂)

[16] The method for producing a cyclic olefin compound according to any one of [1] to [15],
in which the step of producing a cyclic olefin compound is performed while removing the generated cyclic olefin compound to an outside of a reaction system.

This application claims priority on the basis of Japanese Patent Application No. 2020-110761 filed on Jun. 26, 2020, the entire disclosure of which is incorporated herein by reference.

The invention claimed is:

1. A method for producing a cyclic olefin compound, comprising:
a step of producing acyclic olefin compound by decarbonylating and decarboxylating an alicyclic dicarboxylic acid anhydride in presence of a divalent nickel complex represented by General Formula (1),
wherein the divalent nickel complex includes at least one anionic ligand Y represented by any of General Formulae (2) to (7), (X1), and (Y1), Ni(Y)$_m$(L)$_n$ (1)

wherein Ni is divalent nickel, Y is an anionic monodentate or polydentate ligand and has at least one Ni-E covalent bond, E is a heteroatom or a π-bonding group, m is 1 or 2, L is a neutral ligand, and n is a real number of 0 to 6,

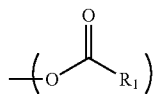

(2)

wherein R₁ is a hydrogen atom or a hydrocarbon group which may have a substituent,

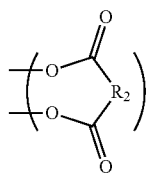

(3)

wherein R₂ is a divalent hydrocarbon group which may have a substituent,

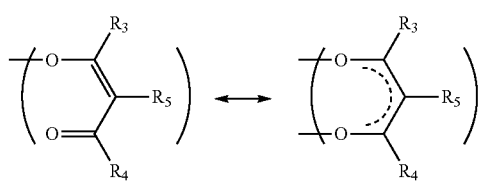

(4)

wherein R₃, R₄, and R₅ are hydrocarbon groups which may have a substituent, R₃ and R₅ or R₄ and R₅ may be bonded to each other to form a ring, and R₃, R₄, and R₅ may be hydrogen atoms,

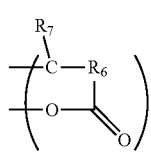

(5)

wherein R₆ is a divalent hydrocarbon group which may have a substituent, R₇ is a hydrogen atom, a hydrocarbon group which may have a substituent, or an oxo group, and in a case where R₇ is a hydrocarbon group, R₇ may be bonded to R₆ to form a ring,

—(Z') (6)

wherein Z' is halogen or OH,

—(Ox) (7)

wherein Ox is an oxoacid selected from NO₃⁻, CO₃²⁻, and PO₄³⁻,

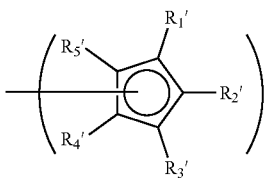
(X1)

wherein $R_1'$, $R_2'$, $R_3'$, $R_4'$, and $R_5'$ are each independently a hydrogen atom or a hydrocarbon group which may have a substituent,

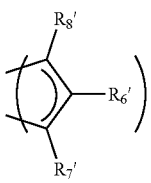
(Y1)

wherein $R_6'$, $R_7'$, and $R_8'$ are each independently a hydrogen atom or a hydrocarbon group which may have a substituent.

2. The method for producing a cyclic olefin compound according to claim 1,
wherein the divalent nickel complex includes at least one anionic ligand Y represented by any of General Formulae (9), (11) to (13), and (Z1), and Formulae (8) and (10),

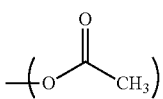
(8)

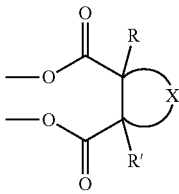
(9)

wherein X is a group of non-metal atoms required to form a ring, and R and R' are each independently a hydrogen atom or a hydrocarbon group which may have a substituent,

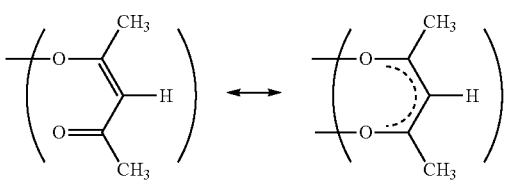
(10)

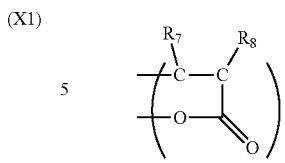
(11)

wherein $R_7$ and $R_8$ are each independently a hydrogen atom or a hydrocarbon group which may have a substituent, and $R_7$ and $R_8$ may be bonded to each other to form a ring,

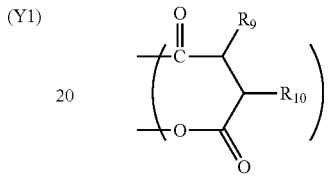
(12)

wherein $R_9$ and $R_{10}$ are each independently a hydrogen atom or a hydrocarbon group which may have a substituent, and $R_9$ and $R_{10}$ may be bonded to each other to form a ring, $$—(Z'') \quad (13)$$

wherein Z" is Cl or Br,

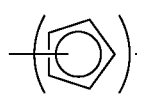
(Z1)

3. The method for producing a cyclic olefin compound according to claim 1,
wherein, in the step of producing a cyclic olefin compound, a compound which can be a ligand for the nickel complex is further present.

4. The method for producing a cyclic olefin compound according to claim 3,
wherein, in the step of producing a cyclic olefin compound, the compound which can be a ligand is present in an amount of 10 to 500 mol with respect to 1 mol of the nickel complex.

5. The method for producing a cyclic olefin compound according to claim 3,
wherein the compound which can be a ligand includes a phosphorus-containing compound.

6. The method for producing a cyclic olefin compound according to claim 3,
wherein the compound which can be a ligand includes at least one selected from a compound represented by General Formula (14) and a compound represented by General Formula (15),

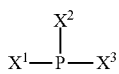

(14)

wherein $X^1$, $X^2$, and $X^3$ are each independently a hydrocarbon group which may have a substituent,

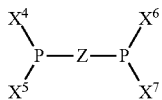

(15)

wherein $X^4$, $X^5$, $X^6$, and $X^7$ are each independently a hydrocarbon group which may have a substituent, and Z is an alkylene group having 1 to 20 carbon atoms, an arylene group having 6 to 20 carbon atoms, a ferrocenylene group, or a binaphthylene group.

7. The method for producing a cyclic olefin compound according to claim 3,
wherein the compound which can be a ligand includes triphenylphosphine.

8. The method for producing a cyclic olefin compound according to claim 1, further comprising:
a step of adding an alcohol compound.

9. The method for producing a cyclic olefin compound according to claim 8,
wherein a boiling point of the alcohol compound is lower than a boiling point of the alicyclic dicarboxylic acid anhydride.

10. The method for producing a cyclic olefin compound according to claim 1,
wherein the alicyclic dicarboxylic acid anhydride includes at least one of a carboxylic acid compound or a carboxylic acid anhydride (excluding the alicyclic dicarboxylic acid anhydride) as an impurity.

11. The method for producing a cyclic olefin compound according to claim 10, further comprising:
a step of adding an alcohol compound; and
a step of contacting the alcohol compound with the impurity in a liquid phase to react the alcohol compound with the carboxylic acid compound or the carboxylic acid anhydride in the impurity, and removing an unreacted alcohol compound.

12. The method for producing a cyclic olefin compound according to claim 11,
wherein a boiling point of the alcohol compound is lower than a boiling point of the alicyclic dicarboxylic acid anhydride.

13. The method for producing a cyclic olefin compound according to claim 1,
wherein the alicyclic dicarboxylic acid anhydride includes a compound represented by General Formula (16), and
the cyclic olefin compound includes a compound represented by General Formula (17),

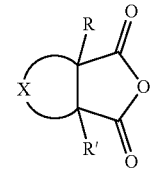

(16)

wherein X is a group of non-metal atoms required to form a ring, and R and R' are each independently a hydrogen atom or a hydrocarbon group which may have a substituent,

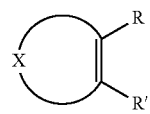

(17)

wherein X is a group of non-metal atoms required to form a ring, and R and R' are each independently a hydrogen atom or a hydrocarbon group which may have a substituent.

14. The method for producing a cyclic olefin compound according to claim 1,
wherein the alicyclic dicarboxylic acid anhydride includes 5,6-benzo-2,3-dicarboxylic acid anhydrides represented by General Formula (18),

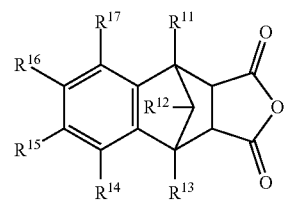

(18)

wherein $R^{11}$, $R^{12}$, $R^{13}$, $R^{14}$, $R^{15}$, $R^{16}$, and $R^{17}$ are each independently a hydrogen atom or a substituent which may have a heteroatom.

15. The method for producing a cyclic olefin compound according to claim 14,
wherein $R^{11}$, $R^{12}$, $R^{13}$, $R^{14}$, $R^{15}$, $R^{16}$, and $R^{17}$ in General Formula (18) are all hydrogens.

16. The method for producing a cyclic olefin compound according to claim 1,
wherein the alicyclic dicarboxylic acid anhydride includes a dicarboxylic acid anhydride represented by General Formula (19),

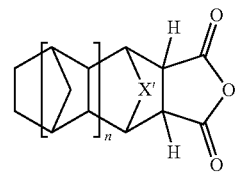

(19)

wherein n is 0 or 1, and X' is O or $CH_2$.

17. The method for producing a cyclic olefin compound according to claim 1,
wherein the step of producing a cyclic olefin compound is performed while removing the generated cyclic olefin compound to an outside of a reaction system.

\* \* \* \* \*